US00PP11140P

United States Patent [19]

Zary

[11] Patent Number: Plant 11,140

[45] Date of Patent: Nov. 30, 1999

[54] FLORIBUNDA ROSE PLANT NAMED 'JACROGEM'

[75] Inventor: Keith W. Zary, Thousand Oaks, Calif.

[73] Assignee: Bear Creek Gardens, Inc., Medford, Oreg.

[21] Appl. No.: 09/066,519

[22] Filed: Apr. 24, 1998

[51] Int. Cl.[6] ..... A01H 5/00

[52] U.S. Cl. ..... Plt./149

[58] Field of Search ..... Plt./148, 149, 150

*Primary Examiner*—Howard J. Locker

*Attorney, Agent, or Firm*—Klarquist Sparkman Campbell Leigh & Whinston

[57] ABSTRACT

Floribunda rose plant having high production of flowers in clusters, the flowers having thick, hard petals and good vase life.

1 Drawing Sheet

The present invention relates to a new and distinct variety of rose plant of the floribunda class which was originated by me by crossing an unnamed seedling with the variety 'JACanne', (U.S. Plant Pat. No. 8,634).

The primary objective of this breeding was to produce a new rose variety having the well shaped flowers and clusters of the unnamed seedling, combined with the hard petals, bright color and clusters of JACanne. The objective was substantially achieved, along with other desirable improvements, as evidenced by the following unique combination of characteristics that are outstanding in the new variety and that distinguish it from its parents, as well as from all other varieties of which I am aware:

1. Flowers presented in clusters of five to seven;
2. High production of cut flowers;
3. Good vase life; and
4. Thick, hard petals.

'JACrogen' is a greenhouse cut flower floribunda rose whose cut flowers can be produced and sold as clusters. Production under California conditions is 160–170 stems/$m^2$ of greenhouse.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (JACpray×Party Girl).

*Pollen parent.*—'JACanne' (U.S. Plant Pat. No. 8,634).

Classification:

*Botanical.*—Rosa hybrida.

*Commerical.*—Floribunda.

FLOWER

Observations made from specimens grown in a greenhouse environment at Somis. Calif., from January 1997 to February 1998.

Blooming habit: Continuous.

Bud:

*Size.*—About 1 inch long when the petals start to unfurl.

*Form.*—Long, pointed ovoid.

*Color.*—When sepals first divide, bud color is Red Group 51B. When half blown, the upper sides of the petals are Red Group 51B, and the lower sides of the petals are Red Group 51B.

*Sepals.*—Color: Green Group 138B. Surface texture: Covered in fine hairs. There are three lightly appendaged sepals. There are two unappendaged sepals with hairy edges.

*Receptacles.*—Color: Green Group 137D. Shape: Funnel. Size: Medium (about 5/16×¼"). Surface: Smooth.

*Peduncle.*—Length: Short (about 1½–2"). Surface: Smooth. Color: Green Green Group 137D. Strength: Stiff, erect.

Bloom:

*Size.*—Small. Average open diameter is about 2½ inches.

*Borne.*—Several together in clusters rounded to flat in shape of five to seven flowers.

*Stems.*—Medium (average about 18–22"), strong.

*Form.*—When first open: High centered. Permanence: Retains its form to the end. Outer petal edges curl slightly.

*Petalage.*—Number of petals under normal conditions: 35.

*Color.*—The upper sides of the petals are Red Group 51B. The reverse sides of the petals are Red Group 51B. The base of each petal has a quite large (¼"×¼"). White Group 155A half moon at the point of attachment. The major color on the upper sides is Red Group 51B.

*Variegations.*—Occasional greenish white streaks on the guard petals.

*Discoloration.*—At the end of the first day: No change. At the end of the third day: No change. By day nine or ten, in the vase, there is a color change toward Red Group 52B. By day twelve, the petals drop.

*Fragrance.*—None.

Petals:

*Texture.*—Thick, leathery.

*Shape.*—Deltoid.

*Form.*—Tips slightly recurved.

*Arrangement.*—Imbricated. Petaloids in the center: Few, small.

*Persistence.*—Petals drop off cleanly before drying.

*Lastingness.*—On the plant: Long (7–8 days). As a cut flower: Long (11–12 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Reddish.

*Stigmas.*—Color: Greenish white.

Plant:

*Form.*—Bush.

*Growth.*—Vigorous; upright; branching. At maturity, in the greenhouse after one year, height is 4½ feet, width is 3½ feet.

Foliage: Number of leaflets on normal mid-stem leaves: Five or seven.

*Size.*—Medium (6" long×4" wide).

*Quantity.*—Abundant.

*Color.*—New foliage: Upper and lower side: Greyed-Purple Group 183B. Old foliage: Upper side: Green Group 139A. Lower side: Green Group 137D.

Leaflets:

*Shape.*—Pointed oval.

*Texture.*—Leathery, glossy.

*Edge.*—Serrated.

*Serration.*—Single, small.

*Petiole rachis.*—Color: Green Group 139A.

*Petiole underside.*—Smooth with occasional prickles.

*Stipules.*—Medium (about ⅝"), serrated.

*Diseases resistance.*—Resistant to mildew under normal growing conditions at Somis, Calif.

Wood:

*New wood.*—Color: Greyed-Purple Group 183A. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium, hooked downward.

*Color when young.*—Greyed-Purple Group 183D.

Small prickles:

*Quantity.*—On main stalks: None. On laterals: None.

I claim:

1. A new and distinct variety of rose plant of the floribunda class, as herein shown and described, characterized particularly by its high production of flowers in clusters, the flowers having thick, hard petals and good vase life.

* * * * *

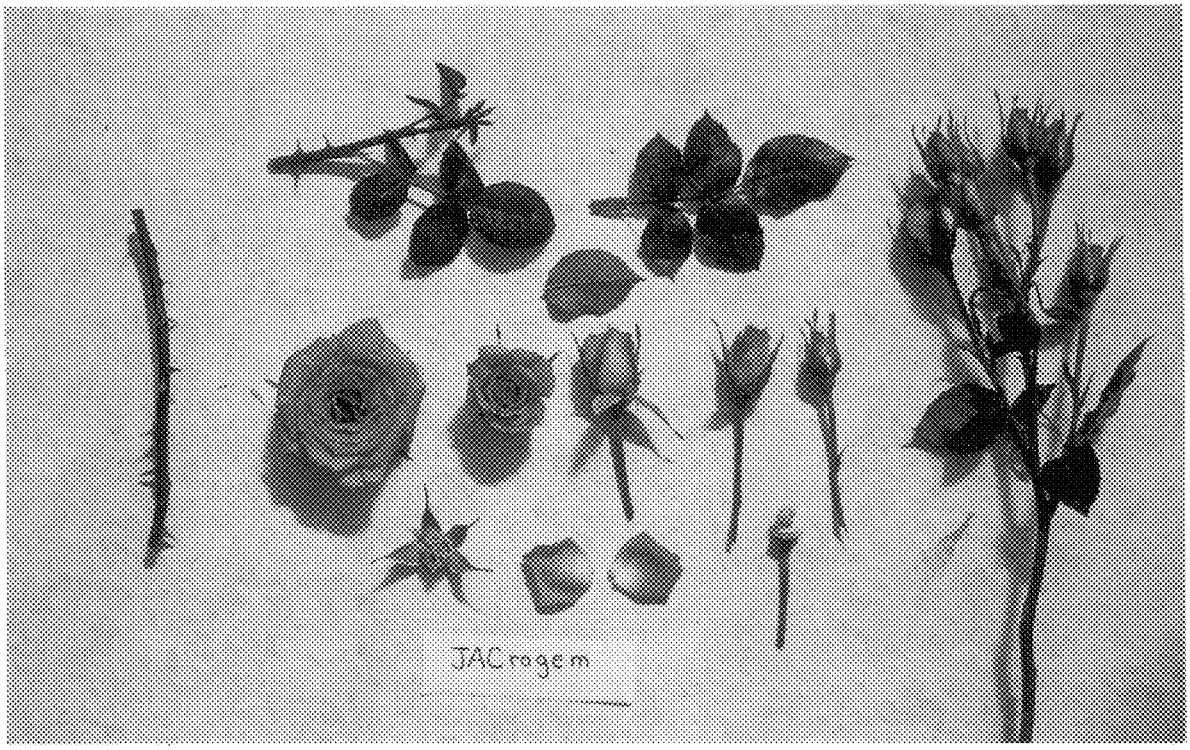
JACrogem